United States Patent [19]

Langdon

[11] 4,408,084

[45] * Oct. 4, 1983

[54] NON-IONIC SURFACTANTS CONTAINING ACETAL GROUPS

[75] Inventor: William K. Langdon, Grosse Ile, Mich.

[73] Assignee: BASF Wyandotte Corporation, Wyandotte, Mich.

[*] Notice: The portion of the term of this patent subsequent to Feb. 19, 1997 has been disclaimed.

[21] Appl. No.: 223,880

[22] Filed: Jan. 9, 1981

[51] Int. Cl.$^3$ ............................ C07C 2/76; C07C 1/00
[52] U.S. Cl. .................................. 568/601; 568/593; 568/603
[58] Field of Search ...................... 568/593, 601, 603

[56] References Cited

U.S. PATENT DOCUMENTS

| | | | |
|---|---|---|---|
| 2,379,703 | 7/1945 | Geltner | 568/613 |
| 2,405,784 | 8/1946 | Geltner | 260/404 |
| 2,786,081 | 3/1957 | Kress | 568/601 |
| 2,796,401 | 6/1957 | Matuszak | 568/601 |
| 2,878,294 | 3/1959 | Kress | 568/601 |
| 2,905,719 | 9/1959 | de Benneville | 568/601 |
| 3,931,337 | 1/1976 | Langdon | 568/601 |
| 4,189,609 | 2/1980 | Langdon | 568/601 |

FOREIGN PATENT DOCUMENTS 2017100  10/1979  United Kingdom ............... 568/601

*Primary Examiner*—John F. Niebling
*Attorney, Agent, or Firm*—Bernhard R. Swick

[57] ABSTRACT

Acetal-coupled non-ionic surfactants are easily degraded into relatively environmentally innocuous fragments having little or no surface activity. The fragments are sufficiently low in molecular weight to be oxidized when exposed to water and atmospheric oxygen. The surface activity can also be destroyed by lowering the alkalinity of the medium in which the non-ionic surfactant is utilized to below pH 7. The non-ionic surfactants of the invention unexpectedly have very low viscosities as compared to surfactants containing a comparable molecular weight and oxyalkylene residue content.

7 Claims, No Drawings

NON-IONIC SURFACTANTS CONTAINING ACETAL GROUPS

BACKGROUND OF THE INVENTION

1. Field of the Invention

This invention relates to biodegradable non-ionic surfactants.

2. Description of the Prior Art

A wide variety of non-ionic surface-active agents are known in the art. Because of their non-ionic nature, these surface-active agents are usually stable in acid, basic and neutral media. Recently, biodegradable polyoxyalkylene copolymer surfactants have been disclosed in U.S. Pat. Nos. 3,931,337 and 4,189,609. These are prepared from individual blocks of polymers and copolymers of alkylene oxides by reaction with formaldehyde or a dialkyl carbonate. The surfactant molecules fragment into individual polyoxyalkylene glycols under the influence of biologic agents or by hydrolysis or when exposed to slightly acidic or basic conditions. Surface-active acetals and formals are disclosed in U.S. Pat. No. 2,905,719. These are ethylene oxide derivatives coupled to the residue of an alkyl alcohol having 8 to 18 carbon atoms utilizing formaldehyde or acetaldehyde. Acid-sensitive non-ionic surface-active compositions are thereby produced which are stable in basic or neutral media. Surface-activity is lost upon treating these non-ionic acetals with an acid.

In U.S. Pat. No. 2,796,401, complex formal lubricating compositions are disclosed which are the reaction product of a monohydric aliphatic or aromatic alcohol, or a glycol with formaldehyde as a coupling agent. The product is made in two stages in which, in the first stage, the hemiformal of the alcohol is made by heating equal moles of the alcohol and formaldehyde. Subsequently, in the second stage, the desired molar proportion of glycol and formaldehyde is added to the hemiformal and reacted to make the desired product.

In U.S. Pat. No. 2,786,081, acetal condensation products are disclosed which are the reaction products of diethylene glycol and formaldehyde. These are useful as plasticizers for polymers including film-forming materials.

SUMMARY OF THE INVENTION

Biodegradable and acid degradable non-ionic surface-active compositions are disclosed containing the residue of a monofunctional organic compound coupled to a polyoxyalkylene glycol derived from alkylene oxides having 2 to 4 carbon atoms. The compositions can contain terminal hydrophobic groups derived from the organic monofunctional alcohols, or carboxylic acids. The aldehyde coupling agent can be any aliphatic aldehyde having up to 4 carbon atoms such as formaldehyde, acetaldehyde, propionaldehyde, and butyraldehyde. Preferably the aldehyde is formaldehyde or acetaldehyde and most preferably the aldehyde is formaldehyde.

The biodegradable nature of the compositions of the invention permits the formation of relatively environmentally innocuous fragments of the surface-active agents of the invention upon exposure to water and atmospheric oxygen. The surface-active agents of the invention can also be split into relatively innocuous fragments upon reducing the pH of the media below 7. The surface-active agents of the invention are particularly useful where it is desired to form an emulsion and then coagulate the emulsion simply by lowering the pH below 7. Unexpectedly, the surface-active agents of the invention have unusually low viscosity. The surfactants of the invention are unexpectedly formed by a selective coupling mechanism in which the monofunctional organic compound is coupled with a polyoxyalkylene glycol as indicated by the water-soluble product obtained, rather than the expected random coupling of each of the reactants such that insoluble species are formed.

DETAILED DESCRIPTION OF THE INVENTION

The polyoxyalkylenes utilized in the preparation of the surface-active agents of the invention are prepared in a conventional manner by reacting an alkylene oxide or mixture thereof with an initiator compound containing at least one active hydrogen atom. Preferably, the initiator compounds have molecular weights of less than 100. Like most surface-active agents, the compounds of the invention are composed of hydrophilic and hydrophobic portions in the same molecule. As is well known in this art, certain alkylene oxides can be employed to provide the hydrophilic portion of the molecule while other alkylene oxides can be employed to produce the hydrophobic portion of the molecule.

The surface-active compounds of the invention have the formula:

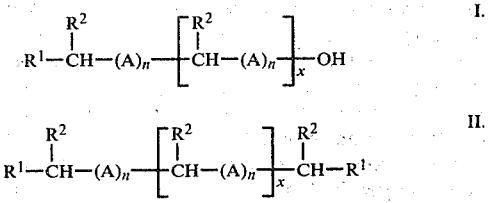

wherein $R^1$ is the residue of at least one hydrophobic monofunctional organic compound derived from a compound selected from the group consisting of an aliphatic alcohol and aliphatic carboxylic acid; an arylalkyl alcohol and carboxylic acid; an alkylarylalkyl alcohol and carboxylic acid; alkoxylated derivatives of each of the forgoing; and an alkoxylated alkylphenol wherein each alkyl group preferably has about 6 to 30 carbon atoms and wherein $R^2$ is hydrogen or alkyl of 1 to 4 carbon atoms, A is the residue of at least one hydrophilic oxyalkylene polymer derived from the same or different alkylene oxides wherein said polymer is selected from at least one of the group consisting of polyalkylene glycols derived respectively from the reaction of an alkylene oxide having 2 carbon atoms or alkylene oxides having 2 to 4 carbon atoms with an active hydrogen compound having at least 2 active hydrogen atoms, x is an integer of 1 to 20, preferably 1 to 10, and n is individually selected from integers such that the molecular weight is about 104 to about 1000.

The surface-active compounds of the invention preferably contain the residue of a monofunctional aliphatic or aromatic compound such as an alkyl alcohol or an alkyl carboxylic acid having 6 to 30 carbon atoms in the alkyl group to provide the hydrophobic portion of the molecule.

The alkylene oxides which can be employed as reactants in the formation of the polyoxyalkylenes are the lower alkylene oxides having 2 to 4 carbon atoms. Examples of such alkylene oxides are ethylene oxide, propylene oxide, the various butylene oxides, and tetrahydrofuran. Mixtures of alkylene oxides can be employed to obtain varying degrees of hydrophobicity and hydrophilicity. The polyoxyalkylene polymers utilized as reactants can have a molecular weight of about 104 to about 1000. Preferably, the molecular weight is about 200 to about 1000. The use of relatively low molecular weight alkylene oxide polymers provides economies in the preparation of surface-active agents in that the reaction time to produce conventional surface-active agents based upon polyoxyalkylenes can be considerably reduced. The use of relatively low molecular weight polyoxyalkylene polymers, coupled in accordance with the process of the invention, also provides readily biodegradable surfactants. Not only do these low molecular weight polyoxyalkylene polymers exhibit relatively little surface-active effects but these low molecular weight polymers are more readily oxidized when exposed to water and atmospheric oxygen. Thus, the surface-active agents of the invention can provide the advantageous surface-active properties of high molecular weight polyoxyalkylene polymer non-ionic surfactants when coupled with an aldehyde in accordance with the process of this invention. When such surfactants are fragmented, such as by reducing the pH of the media in which the surfactant is present to below 7, the individual polyoxyalkylene polymer fragments readily oxidize and can be biodegraded.

The low molecular weight polyoxyalkylene copolymers employed in this invention are generally prepared by carrying out the condensation reaction of the alkylene oxides with an active hydrogen-containing initiator in the presence of an alkaline catalyst in a manner well known to those skilled in the art. Any of the types of catalysts commonly used for alkylene oxide condensation reactions may be employed. Catalysts which may be employed include sodium hydroxide, potassium hydroxide, sodium methylate, sodium ethylate, potassium acetate, sodium acetate, tributylamine and triethylamine. After the condensation reaction is completed, the catalyst may be removed from the reaction mixture by any known procedure such as neutralization, filtration or ion exchange. The condensation is preferably carried out at elevated temperatures and pressures. The condensation products are then subjected to the coupling reaction to form the products of the invention.

The term "active hydrogen atom" is well known to those skilled in the art. It is sufficiently labile to react with ethylene, propylene or butylene oxide and it reacts with methyl magnesium iodide, liberating methane according to the classical Zerewitinoff reaction. The hydrogen atoms are members of a functional group such as a hydroxyl group, a phenol group, a carboxylic acid group, a basic nitrogen group such as an amine group, a hydrazine group, an imine group or an amide group. Hydrogen atoms may be activated by proximity to carbonyl groups such as acetoacetic ester. Examples of active hydrogen initiator compounds, which may be used include ethylene glycol, diethylene glycol, propylene glycol, dipropylene glycol, butylene glycol, amylene glycol, hexylene glycol, heptylene glycol and octylene glycol.

Together with the use of polyoxyalkylene copolymers as hydrophiles, the surface-active compositions of the invention can employ monofunctional hydrophobic aliphatic or aliphatic-aromatic alcohols and carboxylic acids or mixtures thereof as reactants so as to provide terminal hydrophobic groups on the surface-active compounds of the invention. These can be derived from alkyl, alkylaryl, arylalkyl, and alkylarylalkyl alcohols and carboxylic acids. Preferably, the monofunctional alcohols and carboxylic acids have aliphatic groups containing about 6 to about 30 carbon atoms, most preferably about 8 to about 20 aliphatic carbon atoms. The aliphatic groups can be substituted or unsubstituted, saturated or unsaturated.

Examples of useful aliphatic monohydric primary and secondary, normal and branched-chain aliphatic alcohols are n-heptyl alcohol, n-undecyl alcohol, n-dodecyl alcohol, cetyl alcohol, stearyl alcohol, n-nonadecyl alcohol, eicosyl alcohol, ceryl alcohol, palmitoleyl alcohol, 2-methylpentyl alcohol, 3,5-dimethyl-1-hexanol, 4-methyl-2-pentanol, 2,6-dimethyl-4-heptanol, 2,6,8-trimethyl-4-nonanol, n-hexyl alcohol, 2-ethyl-1-butanol, 2-ethyl-1-hexanol, n-octyl alcohol, 2-octyl alcohol, n-nonyl alcohol, n-decyl alcohol, lauryl alcohol, n-tetradecyl alcohol, n-pentadecyl alcohol, octadecyl alcohol, oleyl alcohol, and $C_6$–$C_{20}$ oxo alcohols.

Examples of useful substituted monohydric aliphatic alcohols are as follows: the various glycol mono-esters such as propylene glycol mono-butyl ether, butylene glycol mono-lauryl ether, polypropylene glycol mono-ethers, polybutylene glycol mono-ethers, polytrimethylene glycol mono-ethers; and the various glycol mono-formals such as the mixed formals of glycols and alcohols.

Examples of useful monofunctional aliphatic carboxylic acids useful as reactants in the preparation of the surface-active agents of the invention are as follows: heptylic, caprylic, nonylic, capric, undecylic, lauric, tridecylic, myristic, palmitic, stearic, decenoic, oleic, palmitoleic, linoleic, α-linolenic, and α-eleostearic acids. Examples of useful monofunctional alkylaryl alcohols include the alkoxylated phenols such as 1 to 20 mole propoxylated nonyl and octyl phenol and 1 to 20 mole butoxylated dodecyl phenol. Useful alkylaryl alcohols include 2-phenyl octane. Useful arylalkyl alcohols include 4-(2-ethylphenyl)-1-octane.

Any of the monofunctional alcohols and carboxylic acids set forth above can have substituents which do not contain active hydrogen such as halogen, for example, chlorine, bromine, and iodine, nitrate groups or alkoxy radicals.

The aldehydes utilized to couple the hydrophilic difunctional compounds to the hydrophobic monofunctional compounds, are aliphatic aldehydes generally having 1 to 4 carbon atoms in the hydrocarbon group. Preferably, the aldehydes contain an alkyl chain which has most preferably 1 to 2 carbon atoms. Examples of useful aldehydes are formaldehyde, acetaldehyde, propionaldehyde, and butyraldehyde.

In the preparation of the surface-active compounds of the invention, the reactants are admitted to a reaction zone and reacted in a single stage at reflux temperature in the presence of an acid catalyst and a reaction solvent. Generally, the reaction is carried out at a temperature of about 25° C. to 150° C. Examples of useful acid catalysts are sulfuric acid, hydrochloric acid, hydrobromic acid, paratoluene sulfonic acid, phosphoric acid, trifluoroacetic acid, methane sulfonic acid, and trichloroacetic acid. Preferably sulfuric acid is utilized as the catalyst. The amount of catalyst employed can vary from about 0.01 percent by weight to about 3 percent by weight based upon the total weight of the reactants present. Usually, the reaction is carried out in the presence of a reaction solvent which is an organic solvent which is immiscible with water. The solvent is employed so as to allow removal of the water of reaction by azeotropic distillation. Examples of useful solvents are benzene, toluene, xylene, hexane, and cyclohexane. The time required for the completion of the coupling reaction is generally from about 15 minutes to 10 hours. Preferably, the reaction is completed within 5 hours.

The following examples will further illustrate the method or preparation of the non-ionic, surface-active agents containing acetal groups and their use as surface-active agents. These examples, however, are not to be considered as limiting the scope of the invention. In the specification, claims and examples which follow, all percentages, parts, and proportions are by weight and all temperatures are in degrees centigrade unless otherwise noted.

EXAMPLE 1

Into a one-liter capacity flask equipped with a thermometer, stirrer, and Deak Stark type moisture trap and condenser, there were added 151 grams of a mixture of a fatty alcohol having an average of 12 to 14 carbon atoms in the aliphatic chain sold under the trademark "EPAL 12/85", 480 grams of a polyethylene glycol having a molecular weight of 300, 54 grams of paraformaldehyde and 2 grams of concentrated sulfuric acid together with 200 milliliters of cyclohexane. After starting agitation, the mixture was heated to reflux temperature and water was removed azeotropically over a period of about 2 hours. The catalyst was neutralized with sodium bicarbonate. The residual cyclohexane was then removed by distillation by heating to 130° C. at atmospheric pressure. The mixture was finally stripped at a temperature up to 130° C. at a pressure of approximately 3 millimeters of mercury. The product obtained was cooled to 100° C. and filtered on a coarse sintered glass funnel having a thin bed of diatomaceous earth. Filtration was extremely rapid. The amount of product obtained was 664 grams. The appearance of the product was clear and water-white. The product was further characterized as having a pH of 9.4, a cloud point (1 percent by weight aqueous solution) of greater than 100° C., a surface tension of 34.8 dynes per centimeter at 0.1 percent by weight concentration in water, a Draves sink time of 76.6 seconds at 0.1 percent by weight concentration in water, a specific gravity at 25° C. of 1.021 and a viscosity in centipoise at 25° C. of 240.

EXAMPLE 2

The procedure of Example 1 was repeated utilizing the following reactants: a fatty alcohol having an average of 12 to 15 carbon atoms in the alkyl chain sold under the trademark of "NEODOL 25" in the amount of 305 grams, diethylene glycol 318 grams, paraformaldehyde 100 grams, and concentrated sulfuric acid 2 grams. A product was obtained in the amount of 659 grams having a clear, pale straw appearance, a pH of 7.9, a cloud point (1 percent by weight aqueous solution) of less than 0° C., a surface tension of 32.8 dynes per centimeter at 0.1 percent by weight concentration in water, a Draves sink time of 50.6 seconds at 0.1 percent by weight concentration in water, a specific gravity at 25° C. of 0.978, and a viscosity at 25° C. of 94 centipoise.

EXAMPLE 3

The procedure of Example 1 was repeated substituting the following reactants in the amounts stated. A fatty alcohol having a mixture of carbon chain lengths in the range 12 to 14 carbon atoms sold under the trademark "EPAL 12/85", 189 grams; polyethylene glycol having a molecular weight of 400 in the amount of 405 grams; paraformaldehyde in the amount of 33.3 grams; and concentrated sulfuric acid in the amount of 2 grams. The product was obtained in the amount of 609 grams. It appeared slightly cloudy and had a pH of 8.4. The product was further characterized as having a surface tension of 34.3 dynes per centimeter at 0.1 percent by weight, a Draves sink time of 372 seconds at 0.1 percent by weight concentration in water, a specific gravity at 25° C. of 1.02, and a viscosity at 25° C. of 164 centipoise.

EXAMPLES 4 AND 5

Examples 1 and 3 are repeated substituting a polyoxyalkylene block copolymer derived from the reaction of ethylene oxide and propylene oxide with an active hydrogen compound having 2 active hydrogens.

EXAMPLE 6

Example 1 is repeated subsitutiing a mixture of polyethylene glycol and diethylene glycol for the polyethylene glycol of Example 1.

EXAMPLE 7

Example 1 is repeated sustituting a mixture of diethylene glycol and an oxyalkylene block copolymer derived from the reaction of ethylene oxide and propylene oxide with the polyethylene glycol of Example 1.

EXAMPLE 8

Example 1 is repeated sustituting a mixture of diethylene glycol and a heteric copolymer derived from the reaction of ethylene oxide and propylene oxide with the polyethylene glycol of Example 1.

EXAMPLE 9

Example 1 is repeated sustituting a block copolymer of diethylene glycol and an oxyalkylene block copolymer derived from the reaction of ethylene oxide and propylene oxide with the polyethylene glycol of Example 1.

EXAMPLE 10

Example 1 is repeated sustituting a heteric copolymer of diethylene glycol and an oxyalkylene block copolymer derived from the reaction of ethylene oxide and propylene oxide with the polyethylene glycol of Example 1.

EXAMPLE 11

The procedure of Example 1 was repeated using the following reactants: lauric acid 200 grams, paraformaldehyde 333 grams, polyethylene glycol of 400 molecular weight 405 grams. The product was obtained in the amount of 605 grams. The product had a cloud point of 74° C. (1 percent by weight aqueous solution). Draves sink time was 383 seconds (at 0.1 percent by weight aqueous solution). Surface tension was 31.5 dynes per centimeter (0.1 percent by weight aqueous solution). The viscosity was 196 cps at 25° C.

While this invention has been described with reference to certain specific embodiments, it will be recognized by those skilled in the art that many variations are possible without departing from the scope and spirit of the invention.

The embodiments of the invention in which an exclusive privilege or property is claimed are defined as follows:

1. A composition of matter having the formula:

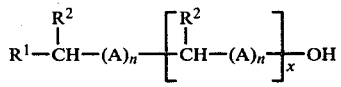

wherein $R^1$ is the residue of at least one hydrophobic monofunctional organic compound derived from a compound selected from the group consisting of an aliphatic alcohol; an alkylarylalkyl alcohol; alkoxylated derivatives of each of the foregoing; and an alkoxylated alkylphenol; wherein $R^2$ is hydrogen or alkyl of 1 to 4 carbon atoms, A is the residue of (1) at least one hydrophilic oxyalkylene polymer derived from different alkylene oxides, or (2) different hydrophilic oxyalkylene polymers, at least one of said polymers being derived from different alkylene oxides wherein said alkylene oxides have 2 to 4 carbon atoms and said polymers are the reaction product of said alkylene oxides with an active hydrogen hydroxyl group-containing compound having at least 2 active hydrogen atoms, x is an integer of 1 to 20, and n is individually selected from integers such that the molecular weight is up to about 1000.

2. A composition of matter having the formula

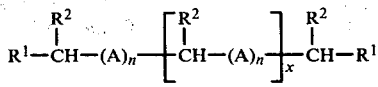

wherein $R^1$ is the residue of at least one hydrophobic monofunctional organic compound derived from a compound selected from the group consisting of an aliphatic alcohol; an arylalkyl alcohol; an alkylarylalkyl alcohol; alkoxylated derivatives of each of the foregoing; and an alkoxylated alkylphenol; wherein $R^2$ is hydrogen or alkyl of 1 to 4 carbon atoms, A is the residue of (1) at least one hydrophilic oxyalkylene polymer derived from different alkylene oxides, or (2) different hydrophilic oxyalkylene polymers, at least one of said polymers being derived from different alkylene oxides wherein said alkylene oxides have 2 to 4 carbon atoms and said polymers are the reaction product of said alkylene oxides with an active hydrogen hydroxyl group-containing compound having at least 2 active hydrogen atoms, x is an integer of 1 to 20 and n is individually selected from integers such that the molecular weight is up to about 1000.

3. The composition of claim 1 or 2 wherein $R^2$ is hydrogen and each alkyl group of said hydrophobic organic compound has about 6 to about 30 aliphatic carbon atoms.

4. The composition of claim 1 or 2 wherein A is the residue of a mixed polyoxyalkylene glycol derived from alkylene oxides having 2 to 4 carbon atoms and each hydrophobic organic compound has about 6 to about 30 aliphatic carbon atoms.

5. The composition of claim 1 or 2 wherein A is a heteric or block polyoxyalkylene glycol derived from alkylene oxides having 2 to 4 carbon atoms and each hydrophobic organic compound has about 6 to about 30 aliphatic carbon atoms.

6. The composition of claim 1 or 2 wherein x is an integer of 1 to 10 and each hydrophobic organic compound has about 6 to about 30 aliphatic carbon atoms.

7. The composition of claim 1 or 2 wherein $R^2$ is hydrogen and A is the residue of a mixed polyoxyalkylene glycol derived from alkylene oxides having 2 to 4 carbon atoms and $R^1$ is the residue of an alkyl alcohol.

* * * * *